(12) United States Patent
Brockmann et al.

(10) Patent No.: US 11,185,365 B2
(45) Date of Patent: Nov. 30, 2021

(54) HIGH-FREQUENCY TOOL FOR MEDICAL RESECTOSCOPES

(71) Applicant: OLYMPUS WINTER & IBE GMBH, Hamburg (DE)

(72) Inventors: Christian Brockmann, Hamburg (DE); Andreas Kaiser, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 458 days.

(21) Appl. No.: 15/754,570

(22) PCT Filed: Oct. 26, 2016

(86) PCT No.: PCT/EP2016/075856
§ 371 (c)(1),
(2) Date: Feb. 22, 2018

(87) PCT Pub. No.: WO2017/076721
PCT Pub. Date: May 11, 2017

(65) Prior Publication Data
US 2018/0235688 A1   Aug. 23, 2018

(30) Foreign Application Priority Data
Nov. 3, 2015 (DE) .................. 10 2015 014 088.4

(51) Int. Cl.
*A61B 18/14* (2006.01)
*A61B 18/00* (2006.01)

(52) U.S. Cl.
CPC .. *A61B 18/149* (2013.01); *A61B 2018/00083* (2013.01); *A61B 2018/00547* (2013.01);
(Continued)

(58) Field of Classification Search
CPC ............ A61B 18/149; A61B 2018/144; A61B 2018/141; A61B 2018/00601;
(Continued)

(56) References Cited

U.S. PATENT DOCUMENTS 2,965,790 A * 12/1960 Ittig ........................ H01J 61/86
313/570
5,007,907 A   4/1991 Nishigaki et al.
(Continued)

FOREIGN PATENT DOCUMENTS

DE          3834230 A1   4/1989
DE    10 2005 032 821 A1   1/2007
(Continued)

OTHER PUBLICATIONS

May 8, 2018 International Preliminary Report on Patentability issued in International Patent Application No. PCT/EP2016/075856.
(Continued)

*Primary Examiner* — Linda C Dvorak
*Assistant Examiner* — Nils A Potter
(74) *Attorney, Agent, or Firm* — Oliff PLC

(57) ABSTRACT

High-frequency (HF) tools are used in medicine for manipulating body tissue, using an HF resectoscope. For electrical insulation of an electrode from an electrode support, the ends of the electrode are initially guided through ceramic tubes. These ceramic tubes are sensitive in particular to forces transverse to the longitudinal axis of the resectoscope. Disclosed herein is a high-frequency tool that has increased stability with respect to transverse forces. An electrode has two ends, which for establishing a connection to an electrode support are each insertable into a receiving opening of the ends of the electrode support, or positionable in front of the ends. The electrode is contacted in an electrically conductive
(Continued)

manner, at least in the area of a receiving opening, with a conductor wire that is guided in the electrode support.

15 Claims, 2 Drawing Sheets

(52) U.S. Cl.
CPC ............... *A61B 2018/00601* (2013.01); *A61B 2018/141* (2013.01); *A61B 2018/144* (2013.01)

(58) Field of Classification Search
CPC ........... A61B 2018/00547; A61B 2018/00083; A61B 2018/1405
USPC .......................................................... 606/46
See application file for complete search history.

(56) References Cited

U.S. PATENT DOCUMENTS

| | | | | |
|---|---|---|---|---|
| 5,919,189 | A | * | 7/1999 | Benderev ............. A61B 18/149 606/41 |
| 6,030,383 | A | | 2/2000 | Benderev |
| 6,033,400 | A | | 3/2000 | Grossi et al. |
| 2002/0000268 | A1 | * | 1/2002 | Miyamoto .............. F01N 13/16 148/421 |
| 2005/0251134 | A1 | * | 11/2005 | Woloszko ............ A61B 18/149 606/46 |
| 2006/0050143 | A1 | * | 3/2006 | Ouchi ................ A61B 18/1492 348/65 |
| 2008/0077129 | A1 | * | 3/2008 | Van Wyk ............. A61B 18/149 606/46 |
| 2011/0106072 | A1 | * | 5/2011 | Sundquist .............. A61B 18/16 606/41 |
| 2014/0088592 | A1 | | 3/2014 | Van Wyk et al. |

FOREIGN PATENT DOCUMENTS

| | | |
|---|---|---|
| EP | 1 072 230 A1 | 1/2001 |
| JP | S62-122651 A | 6/1987 |
| JP | H10-295701 A | 11/1998 |
| JP | 2000-511077 A | 8/2000 |

OTHER PUBLICATIONS

Jan. 16, 2017 International Search Report issued in International Patent Application No. PCT/EP2016/075856.

* cited by examiner

HIGH-FREQUENCY TOOL FOR MEDICAL RESECTOSCOPES

TECHNICAL FIELD

The invention relates to a high-frequency tool for medical resectoscopes for manipulation of body tissue.

BACKGROUND

High-frequency (HF) tools are used in medicine for manipulating body tissue, for example the removal of tissue. Typical applications are found in urology, where they are used in prostate resection, for example. The high-frequency tool may be an HF cutting electrode that is connected to a high-frequency generator, wherein the generator may be switched on an off by an operator, using a switch.

When the high frequency is switched on, a cutting loop situated on the HF cutting electrode makes a very light cut, essentially without resistance, through the body tissue to be removed. For cutting the tissue, by use of the high-frequency tool or cutting electrode an electrode support of the resectoscope is moved axially forward or backward with respect to the resectoscope. Thus, forces act on the tool or on the cutting loop essentially in parallel to the axial direction of the resectoscope.

In known cutting electrodes, the two ends of the cutting loop are connected to the HF generator via conductive wires, for example. For the electrical connection to the generator, the conductive wires are initially led through a forked tube having two ends; the forked tube may then converge toward the loop support or electrode support as a single tube. This electrode support extends in the direction of the proximal end of the resectoscope, in particular toward a slide of the resectoscope, where the conductive wires are connectable to the generator in a known manner.

For electrical insulation with respect to the electrode support, the conductive wire or the conductive wires is/are sheathed with an insulator, for example an insulating tube or a plastic tube. The areas of the cutting electrode or the ends of the cutting loop provided with the insulator are initially led through a ceramic tube in each case before they are guided into the electrode support. These ceramic tubes are placed in or on a holder at the ends of the electrode support. The ceramic tubes are used primarily for stabilizing the temperature as a result of the heat that is generated by the HF generator at the electrode. In addition, the ceramic tubes mechanically stabilize the electrode.

In particular for treatment procedures such as enucleation, the above-described design of an electrode or cutting electrode has proven to be disadvantageous, since the forces that act during the enucleation are much greater compared to forces that act during tissue resection. In the treatment methods stated by way of example, forces act on the electrode not only in the axial direction of the resectoscope, but also transversely thereto. The ceramic tubes may break, in particular as a result of these transverse forces. In addition to the mechanical instability of the electrode thus caused, a short circuit between the electrode, the conductive wires, and the electrode support of the electrode may also occur within the electrode. Use of the above-described cutting electrode is thus limited to applications in which forces occur only in the axial direction of the resectoscope, with no additional, or only slight, transverse forces. In the prior art, this problem is currently addressed by providing a bracket, which absorbs the mechanical forces, in order to stabilize the cutting loop. A drawback is that the additional bracket restricts visibility and limits use of the cutting blade.

SUMMARY

On this basis, the object of the invention is to provide a high-frequency tool for a medical resectoscope, which has increased stability in particular with respect to transverse forces.

Disclosed here in is a high-frequency tool for medical resectoscopes for achieving the above-mentioned object. Accordingly, it is provided according to the invention that the electrode has two ends that are each positionable in, or, viewed in the distal direction, in front of, a receiving opening in the ends of the electrode support in order to establish a connection with the electrode support, and the electrode is contacted in an electrically conductive manner, at least in an area around a receiving opening, with a conductor wire that is guided in the electrode support and whose cross section is smaller than the cross section of the electrode. As a result of the two ends of the high-frequency tool, in particular designed as a bracket-like cutting loop, or the electrode being inserted directly into the receiving openings of the electrode support, additional stabilizing ceramic tubes may be dispensed with. The high-frequency tool according to the invention thus has increased stability with respect to transverse forces. The ends of the high-frequency tool may be electrically insulated from the electrode support. Likewise, the conductor wire(s) connected to the high-frequency tool may be electrically insulated from the electrode support. The electrode support is metallic or metal-plated or designed as an insulator. In addition, it may be provided according to the invention that the ends of the electrode are connected to the conductor wire in front of the receiving openings by means of crimping pliers. The cross section of the conductor of the electrode may be between 0.05 mm$^2$ and 1.8 mm$^2$, in particular 0.2 mm$^2$ to 0.8 mm$^2$, preferably 0.4 mm$^2$. Due to the enlarged cross section of the conductor of the electrode, the electrode may be connected to the holders of the electrode support in a more stable manner. The electrode has increased mechanical stability with respect to transverse forces, simply due to the increased cross section of the conductor of the electrode.

In particular, the present invention further provides that the ends of the electrode support, in particular of the forked tube, are widened to accommodate the ends of the electrode, preferably the cutting loop, in particular that the ends are designed as widened areas. In particular, the holders or the widened areas of the ends of the electrode support are also designed so that they are able to accommodate the ends of the electrode together with the insulation that sheathes the ends of the electrode. The openings or widened areas on the electrode support are dimensioned in such a way that the insulated ends of the electrode have little or no play. It is provided in particular that the insulated ends of the electrode must be pushed or pressed into the openings in the electrode support. As the result of this fastening of the electrode to the forked tube, the electrode is able to withstand loads from transverse forces in particular, without mechanical damage to the electrode.

It may preferably also be provided that the electrode and the conductor wire are designed as one piece from an electrically conductive material, the electrode preferably representing an area of the conductive wire having an enlarged cross section. Particularly high stability may be achieved due to this one-piece design, since the electrode and the conductor wire can no longer be inadvertently separated from one another by the action of external forces, in particular transverse forces.

Furthermore, the present invention may provide that the conductor wire has a continuous design, in particular is guidable from one receiving opening to the other receiving opening, and the electrode, as a tube, is guided between the ends of the electrode support above the conductor wire. The internal diameter of the tube is to be selected in such a way that there is preferably continuous conductive contact between the tube and the conductor wire. Since the tube is thus guided via the conductor wire, increased stability may be achieved due to the fact that the tube is inseparably connected to the conductor wire.

In particular, it may be conceivable according to the invention for the ends of the electrode (13) to be sheathed with a construction material having a strength greater than 80 MPa. Another advantageous exemplary embodiment of the present invention may provide that the ends of the electrode are sheathed by an insulator, in particular a plastic tube, preferably a PTFE tube. In addition, it is conceivable for the tube to be made of any given insulating material that may be placed tightly against the electrode. The wall thickness of the insulating tube may be 0.1 mm to 0.5 mm, in particular 0.1 mm to 0.3 mm, preferably 0.2 mm.

Another particularly preferred exemplary embodiment of the present invention may provide that the ends of the electrode are each electrically insulated from the ends of the electrode support by PEEK tubes or PPS tubes. These PEEK tubes may insulate the ends of the electrode from the ends of the electrode support, as an alternative or in addition to the insulating tube. The PEEK tubes further stabilize the electrode since PEEK has a high mechanical strength, in particular with respect to transverse forces.

The present invention may also preferably provide that the ends of the electrode are mechanically fixedly connected to the conductor wires, in particular welded, soldered, clamped, crimped, or the like. It is also conceivable for the ends of the electrode and the guide wires to be joined together by means of crimping pliers. Due to this fixed connection of the electrode to the conductor wires, the electrode is stable in particular with respect to forces in the axial direction. In addition, the electrode may be pulled by the conductive wires into the holders or widened areas of the electrode support, thus allowing further stabilization of the electrode.

In particular, the present invention further provides that the insulation of the ends of the electrode and of the wires is one piece, preferably composed of multiple pieces. The advantage of one-piece insulation is that the insulation is continuous without interruption. Due to the unavoidable interruptions in multi-piece insulation, it is possible, for example, for liquids such as salt solutions or the like to approach the conductors, resulting in a short circuit. One advantage of multi-piece insulation may be seen in the fact that different insulators or different insulator thicknesses may be used for different conductor sections. Areas that are exposed to increased mechanical load may, for example, be provided with a thicker insulating tube. Thus, for example, it may be provided that the ends of the electrode as well as the individual conductive wires are provided with an insulating tube. Alternatively, it is conceivable for the ends of the electrode and of the respective conductive wire to be electrically insulated from the walls of the electrode support or of the forked tube by a single insulating tube.

Furthermore, the invention may provide that the ends of the electrode sheathed by the insulation are fixedly connected, in particular crimped, glued, or the like, in the widened areas of the electrode support. The required increased stability of the electrode with respect to transverse forces may be achieved due to this rigid connection of the electrode to the electrode support or the forked tube.

Another exemplary embodiment of the present invention may provide that for stabilization, the ends of the electrode are insertable through steel tubes situated directly in front of the openings of the electrode support. It may be conceivable for the metal tubes to be an integral part of the electrode or of the ends of the electrode support. The insulation for the electrode is then once again guidable via the additional tubes or through the tubes. It is thus conceivable for insulated tubes, as an integral part of the electrode, to be insertable into widened areas of the electrode support. It would thus be possible to enlarge the contact surface between the electrode and holder for the electrode support. The forces acting on the electrode may be better distributed or compensated for due to enlarging the contact surface, resulting in increased stability.

BRIEF DESCRIPTION OF THE DRAWINGS

One preferred exemplary embodiment of a high-frequency tool is described in greater detail below with reference to the drawings, which show the following.

DETAILED DESCRIPTION

Figure 1:
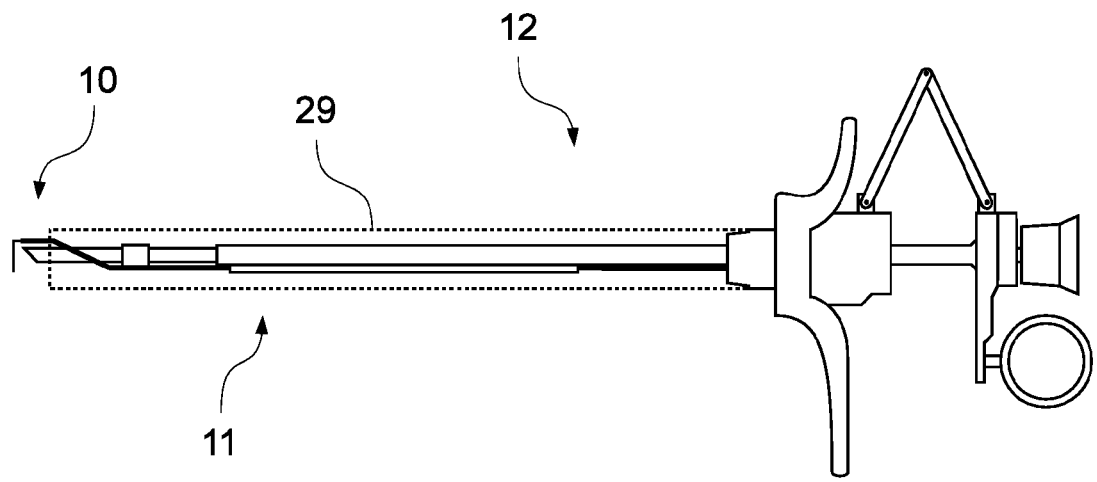
FIG. 1 shows an HF resectoscope with a high-frequency tool.
Figure 2:
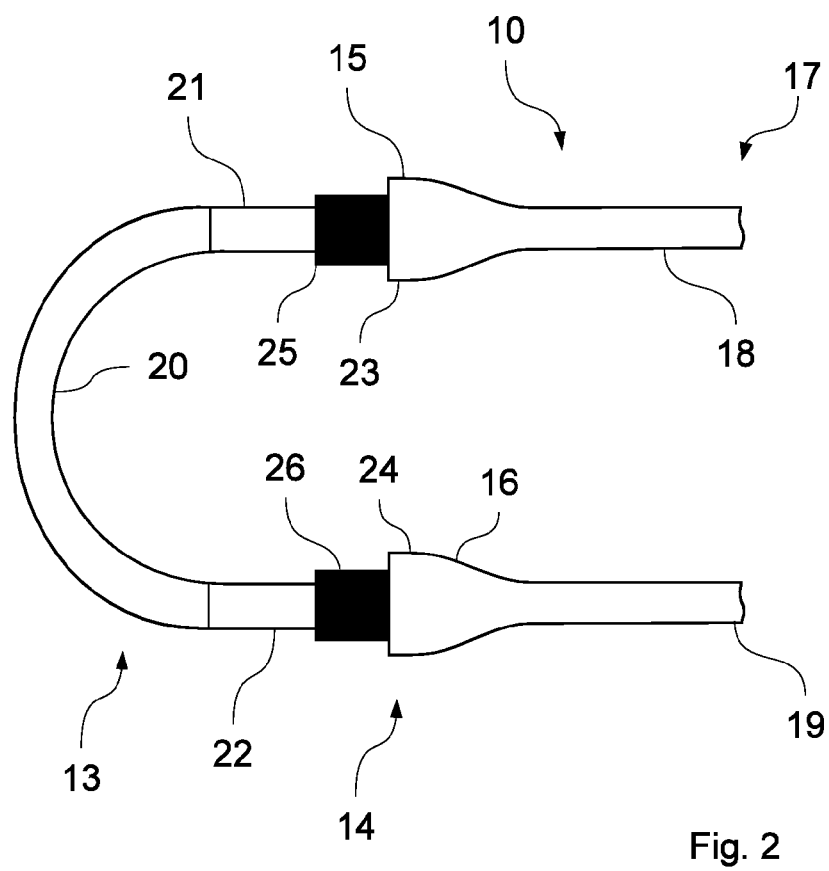
FIG. 2 shows a view of a distal area of an electrode.
Figure 3:
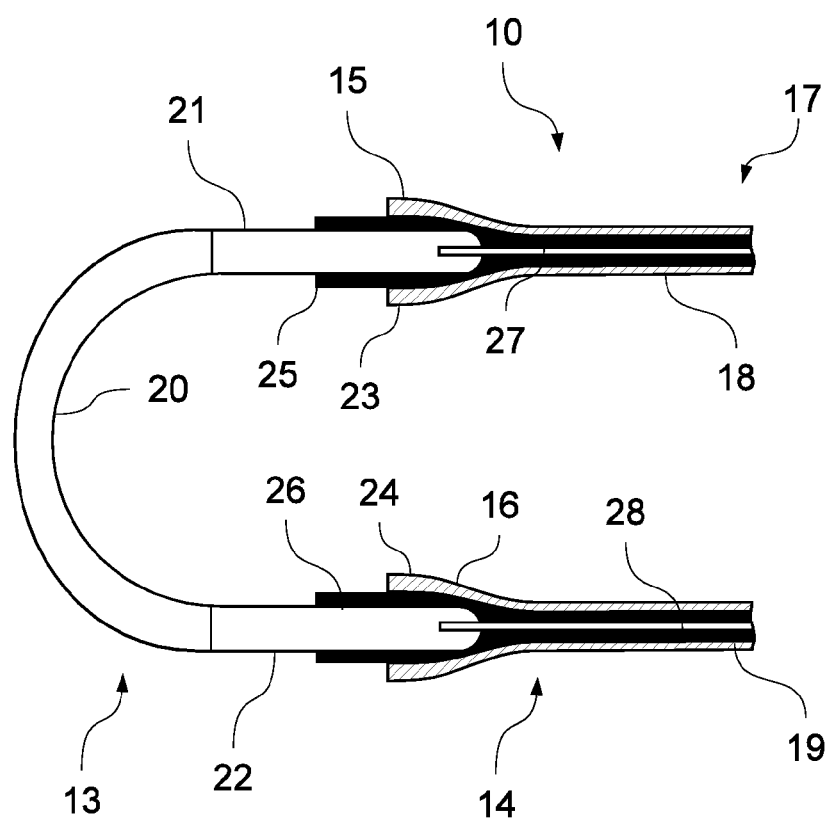
FIG. 3 shows a cross section of the electrode according to FIG. 2.

The high-frequency tool 10 according to the invention is situated on a distal end of a shank 11 of a resectoscope 12. An HF resectoscope 12 or a carrier of an HF resectoscope 12 is illustrated in FIG. 1 with an indicated outer shank 29 by way of example. In FIG. 1, the high-frequency tool 10 is in a working position, in which it is pushed out from the outer shank 29. The high-frequency tool 10 illustrated in FIGS. 1, 2, and 3 is designed by way of example as a cutting electrode having a cutting loop. It is expressly noted at this point that the present invention is not limited to the exemplary embodiment of a resectoscope 12 or a cutting electrode illustrated here. Rather, the high-frequency tool 10 according to the invention may be used for any medical instrument.

Since the high-frequency tool 10 is regarded as the subject matter of the present invention, further description of the illustrated resectoscope 12 is dispensed with. Reference is made to the extensive prior art for a more detailed description.

FIG. 2 illustrates an enlarged detail of the high-frequency tool 10 according to the invention. This high-frequency tool 10 essentially comprises a bracket-like electrode 13 and the electrode support 14. Of the electrode support 14, only two ends 15, 16 are illustrated in FIG. 2. The electrode support 14 is illustrated by a forked tube 17, likewise only partially shown. The forked tube 17 has two tubular arms 18, 19 that converge into a single tube, and which together form the electrode support 14.

The electrode 13 illustrated here has a bow 20 or bracket that extends downwardly into the plane of the drawing. However, it is also conceivable for this bow 20 to be designed as a simple connection of the ends 21 and 22, and to lie in the same plane as the ends. The cutting depth or the cutting pattern may be specified due to the design of the bow 20.

For fastening the electrode 13 to the forked tube 17 or to the electrode support 14, the ends 21, 22 are inserted into an opening or widened area 23, 24 at the ends 15, 16, respectively, of the electrode support 14. Since the electrode 13 as well as the arms 18, 19 of the forked tube 17 or of the electrode support 14 may be metallic, the likewise metallic electrode 13 or the ends 21, 22 of the electrode 13 must be insulated from the widened areas 23, 24. For this purpose, the invention provides for sheathing the end 21 and the end 22 with an insulating tube 25, 26, respectively. This insulating tube 25, 26 may be a plastic tube or a PTFE tube, for example. The wall thickness of this tube may be 0.1 mm to 0.5 mm or 0.2 mm to 0.4 mm, in particular 0.3 mm, the wall thickness being a function primarily of the material and the required impact strength.

The ends 21, 22 of the electrode 14 are each fixedly connected to a conductor wire 27, 28. This fixed connection between the ends 21, 22 and the conductor wires 27, 28 may be a crimped, soldered, or plug-in connection or the like.

The conductor wires 27, 28 are electrically insulated from the walls of the arms 18, 19 by insulation in the same way as for the ends 21, 22. As illustrated in FIG. 3, this insulation may involve the same insulating tubes 25, 26 as those which electrically insulate the ends 21, 22. The insulating tubes 25, 26 then converge into one insulating tube.

The high-frequency tool 10 is inserted with its ends 21, 22 into the widened areas 23, 24 in such a way that the ends 21, 22 together with the insulating tubes 25, 26 form an essentially fixed connection to the widened areas 23, 24. The high-frequency tool 10 according to the invention is stable with respect to transverse forces due to this plug-in connection between the electrode 13 and the conductor wires 27, 28. That is, in particular the widened areas 23, 24 of the electrode support 17 and the electrode 13 are not mechanically damaged when force is exerted transversely with respect to the longitudinal axis of the resectoscope 12.

It is quite conceivable and within the scope of the invention to provide that the arms 18, 19 or the widened areas 23, 24 of the electrode support 17 illustrated in FIGS. 2 and 3 have a different shape. In addition, it is provided according to the invention that instead of the insulating tubes 25, 26 or in addition to the insulating tubes 25, 26, the ends 21, 22 of the electrode 14 may be insulated from the electrode support 17 by additional or alternative insulators, for example PEEK tubes.

LIST OF REFERENCE NUMERALS

10 high-frequency tool
11 shank
12 resectoscope
13 electrode
14 electrode support
15 end
16 end
17 forked tube
18 arm
19 arm
20 bow
21 end
22 end
23 widened area
24 widened area
25 insulating tube
26 insulating tube
27 conductor wire
28 conductor wire
29 outer shank

The invention claimed is:

1. A high-frequency tool for medical resectoscopes for manipulation of body tissue, comprising:
    an electrode support that is movable in an axial direction of the resectoscope and includes distal, fork-shaped ends, and
    an electrode which may be acted on with high-frequency current and which is mounted on the distal, fork-shaped ends of the electrode support,
    wherein:
        the electrode has two ends, which for establishing a connection to the electrode support are each positioned in, or, viewed in a distal direction, in front of, a receiving opening of the ends of the electrode support,
        the ends of the electrode support include widened areas that are wider than other areas of the ends of the electrode support to accommodate the ends of the electrode,
        the electrode is contacted in an electrically conductive manner, at least in an area around the receiving opening, with a conductor wire that is guided in the electrode support and has a cross-sectional dimension that is smaller than a cross-sectional dimension of the electrode,
        the two ends of the electrode are positioned in the receiving opening in the ends of the electrode support so as to not extend proximally of the widened areas, and
        the two ends of the electrode are sheathed by an insulator, the insulator being disposed within the fork-shaped ends of the electrode support and including widened areas that are wider than other areas of the insulator to accommodate the ends of the electrode.

2. The high-frequency tool according to claim 1, wherein the electrode and the conductor wire are made of an electrically conductive material in one piece.

3. The high-frequency tool according to claim 1, wherein the conductor wire has a continuous design, and the electrode is a tube that is guided between the ends of the electrode support above the conductor wire.

4. The high-frequency tool according to claim 1, wherein the ends of the electrode are sheathed with a construction material having a strength greater than 80 MPa.

5. The high-frequency tool according to claim 1, wherein the insulator comprises PEEK tubes or PPS tubes that are configured to electrically insulate the ends of the electrode from the ends of the electrode support.

6. The high-frequency tool according to claim 1, wherein the ends of the electrode are mechanically fixedly connected to the conductor wire.

7. The high-frequency tool according to claim 1, wherein the insulator sheaths the ends of the electrode and ends of the conductive wire and is designed as one piece.

8. The high-frequency tool according to claim 1, wherein the ends of the electrode are fixedly connected to the widened areas of the electrode support.

9. The high-frequency tool according to claim 1, wherein for stabilization, the ends of the electrode are insertable through steel tubes situated directly in front of the receiving openings of the electrode support.

10. The high-frequency tool according to claim 9, wherein the tubes form a part of the electrode or of the ends of the electrode support.

11. The high-frequency tool according to claim 1, wherein the widened areas are disposed at distal-most ends of the electrode support.

12. The high-frequency tool according to claim 1, wherein the receiving opening is formed in the widened areas of the electrode support, and the receiving opening has a larger width than a width of an inner lumen extending through the distal, fork-shaped ends of the electrode support at a position proximal of the widened areas.

13. The high-frequency tool according to claim 1, wherein the electrode is a tube, and the conductor wire has a continuous design so as to extend from one end to an other end of the electrode support inside the tube.

14. The high-frequency tool according to claim 1, wherein the widened areas of the ends of the electrode support have a length extending along the ends of the electrode support that is shorter than a length of the other areas of the ends of the electrode support.

15. The high-frequency tool according to claim 1, wherein the widened areas of the insulator overlap the widened areas of the ends of the electrode support.

* * * * *